US010288019B2

(12) United States Patent
Jammoussi et al.

(10) Patent No.: US 10,288,019 B2
(45) Date of Patent: May 14, 2019

(54) SECONDARY SYSTEM AND METHOD FOR CONTROLLING AN ENGINE

(71) Applicant: Ford Global Technologies, LLC, Dearborn, MI (US)

(72) Inventors: Hassene Jammoussi, Canton, MI (US); Imad Hassan Makki, Dearborn Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 259 days.

(21) Appl. No.: 15/216,409

(22) Filed: Jul. 21, 2016

(65) Prior Publication Data
US 2018/0023523 A1    Jan. 25, 2018

(51) Int. Cl.
| | | |
|---|---|---|
| *G01M 17/00* | (2006.01) | |
| *G06F 7/00* | (2006.01) | |
| *G06F 19/00* | (2018.01) | |
| *F02M 35/09* | (2006.01) | |
| *F02M 35/024* | (2006.01) | |
| *F02M 35/10* | (2006.01) | |
| *F02M 35/104* | (2006.01) | |
| *G01N 15/08* | (2006.01) | |
| *B01D 46/44* | (2006.01) | |
| *B01D 46/00* | (2006.01) | |

(52) U.S. Cl.
CPC .......... *F02M 35/09* (2013.01); *F02M 35/024* (2013.01); *F02M 35/104* (2013.01); *F02M 35/1038* (2013.01); *G01N 15/08* (2013.01); *B01D 46/0086* (2013.01); *B01D 46/446* (2013.01); *G01N 2015/084* (2013.01)

(58) Field of Classification Search
None
See application file for complete search history.

(56) References Cited

U.S. PATENT DOCUMENTS

| | | | |
|---|---|---|---|
| 7,444,234 B2 | 10/2008 | Bauerle | |
| 8,327,695 B2 | 12/2012 | Jackson et al. | |
| 8,626,456 B2 * | 1/2014 | Moore | F02D 41/18 702/184 |
| 2016/0370799 A1 * | 12/2016 | Denton | G05B 13/0265 |

* cited by examiner

*Primary Examiner* — Abby Y Lin
*Assistant Examiner* — Kenny A. Taveras
(74) *Attorney, Agent, or Firm* — Julia Voutyras; McCoy Russell LLP (57) ABSTRACT

Systems and methods for evaluating whether or not degradation of an engine air intake air filter is present based on a pressure drop across the air filter are presented. In one example, a mean and standard deviation of a pressure drop across an air filter are a basis for indicating whether or not the air filter is degraded. Further, the mean and standard deviation are a basis for estimating a useful life cycle of the air filter.

20 Claims, 4 Drawing Sheets

SECONDARY SYSTEM AND METHOD FOR CONTROLLING AN ENGINE

FIELD

The present description relates to a system and methods for diagnosing and mitigating the effects of a clogged engine air filter. The system and methods provide may diagnose air filter operation during steady state and transient air flow conditions through the engine air filter.

BACKGROUND AND SUMMARY

An air intake of an internal combustion engine may include an air filter so that debris may not be drawn to an engine where the debris could cause engine degradation. The air filter may be position in an engine air intake upstream of a throttle so air entering the engine is filtered as soon as it enters the engine air intake. One way to estimate whether or not an air filter is degraded is to determine an air pressure drop across the air filter at a steady air flow amount through the air filter. However, a driver of a vehicle may often change the engine torque demand to meet driving conditions. An increasing driver demand torque may increase air flow through the air filter while a decreasing driver demand torque may decrease air flow through the air filter. Such torque and air flow changes may occur frequently so that establishing constant air flow through the air filter may be difficult and infrequent. As a result, reliable estimates of air filter performance may be delayed while debris continues to accumulate in the air filter. As a result, engine performance may degrade before conditions are established where the air filter may be reliably diagnosed.

The inventors herein have recognized the above-mentioned limitations and have developed an engine air filter diagnostic method, comprising: indicating via a controller, engine air filter degradation in response to a mean of a pressure change across an engine air filter, the pressure change across the engine air filter based on data observed via the controller during transient air flow conditions through the engine air filter.

By judging the presence or absence of engine air filter degradation in response to a mean of a pressure change across the engine air filter, it may be possible to provide the technical result of evaluating an engine air filter during transient air flow conditions through the engine air filter. In particular, a mean and a standard deviation of a pressure change across an engine air filter may be a basis for determining and indicating engine air filter degradation. The mean and standard deviation may be determined based on data taken during steady state or transient air flow through the air filter. Consequently, air filter degradation may be evaluated over a wider range of engine operating conditions so that a driver of a vehicle may be timely notified of air filter degradation.

The present description may provide several advantages. In particular, the approach may provide more timely notification of engine air filter degradation. In addition, the approach may provide an indication that engine power is reduced. Further, the approach may provide an estimate of a remaining useful life cycle so that a driver may know when an air filter is approaching a degraded state.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The advantages described herein will be more fully understood by reading an example of an embodiment, referred to herein as the Detailed Description, when taken alone or with reference to the drawings, where.

DETAILED DESCRIPTION

Figure 1:
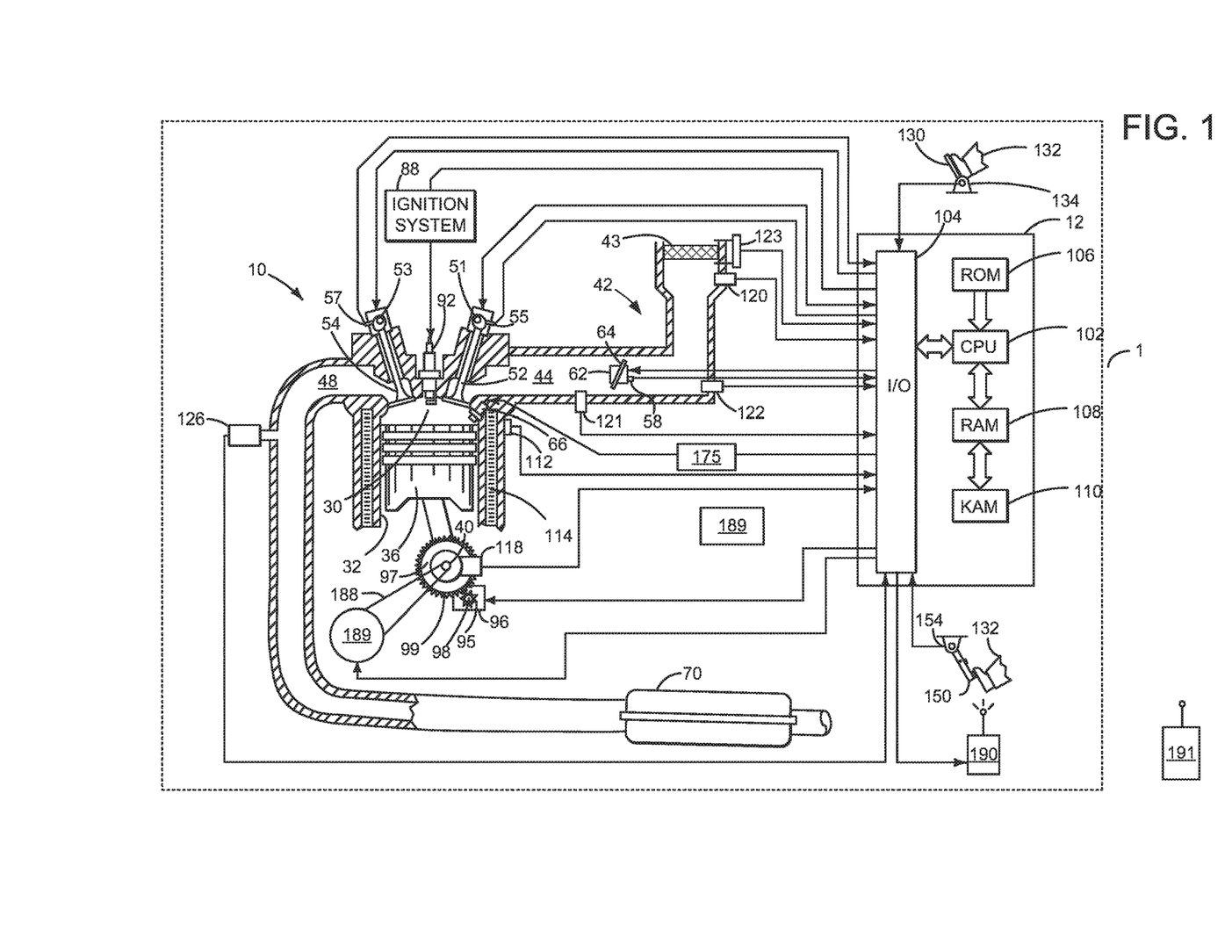
FIG. 1 is a schematic diagram of an engine in a vehicle.

The present description is related to diagnosing degradation of an engine air intake filter. The engine air intake filter may be included in a vehicle with an engine as is shown in FIG. 1. The air filter may exhibit operating characteristics shown in the plots of FIGS. 2 and 3. An example engine air filter diagnostic is shown in FIG. 4. The diagnostic shown in FIG. 4 may be provided according to the method of FIG. 5 in cooperation with the system shown in FIG. 1.

Referring to FIG. 1, internal combustion engine 10, comprising a plurality of cylinders, one cylinder of which is shown in FIG. 1, is controlled by electronic engine controller 12. Engine 10 includes combustion chamber 30 and cylinder walls 32 with piston 36 positioned therein and connected to crankshaft 40. Flywheel 97 and ring gear 99 are coupled to crankshaft 40. Starter 96 includes pinion shaft 98 and pinion gear 95. Pinion shaft 98 may selectively advance pinion gear 95 to engage ring gear 99. Starter 96 may be directly mounted to the front of the engine or the rear of the engine. In some examples, starter 96 may selectively supply torque to crankshaft 40 via a belt or chain. In one example, starter 96 is in a base state when not engaged to the engine crankshaft.

Combustion chamber 30 is shown communicating with intake manifold 44 and exhaust manifold 48 via respective intake valve 52 and exhaust valve 54. Each intake and exhaust valve may be operated by an intake cam 51 and an exhaust cam 53. The position of intake cam 51 may be determined by intake cam sensor 55. The position of exhaust cam 53 may be determined by exhaust cam sensor 57. Intake cam 51 and exhaust cam 53 may be moved relative to crankshaft 40.

Fuel injector 66 is shown positioned to inject fuel directly into cylinder 30, which is known to those skilled in the art as direct injection. Alternatively, fuel may be injected to an intake port, which is known to those skilled in the art as port injection. Fuel injector 66 delivers liquid fuel in proportion to the pulse width of signal from controller 12. Fuel is delivered to fuel injector 66 by a fuel system 175. In addition, intake manifold 44 is shown communicating with optional electronic throttle 62 (e.g., a butterfly valve) which adjusts a position of throttle plate 64 to control air flow from air filter 43 and air intake 42 to intake manifold 44. Throttle 62 regulates air flow from air filter 43 in engine air intake 42 to intake manifold 44. In one example, a high pressure, dual stage, fuel system may be used to generate higher fuel pressures. In some examples, throttle 62 and throttle plate 64 may be positioned between intake valve 52 and intake manifold 44 such that throttle 62 is a port throttle.

A pressure difference across air filter 43 may be determined via differential pressure sensor 123. Alternatively, pressure sensor 120 may determine pressure on a downstream side of air filter 43 while barometric pressure may be estimated to determine a pressure drop across air filter 43.

Distributorless ignition system 88 provides an ignition spark to combustion chamber 30 via spark plug 92 in response to controller 12. Universal Exhaust Gas Oxygen (UEGO) sensor 126 is shown coupled to exhaust manifold 48 upstream of catalytic converter 70. Alternatively, a two-state exhaust gas oxygen sensor may be substituted for UEGO sensor 126.

Converter 70 can include multiple catalyst bricks, in one example. In another example, multiple emission control devices, each with multiple bricks, can be used. Converter 70 can be a three-way type catalyst in one example.

Engine 10 is also shown coupled to electric machine 189, which may be a belt driven integrated starter/alternator. Belt 188 mechanically couples electric machine 189 to crankshaft 40. Alternatively, electric machine may be directly coupled to crankshaft 40 or in mechanical communication with crankshaft 40.

Controller 12 is shown in FIG. 1 as a conventional microcomputer including: microprocessor unit 102, input/output ports 104, read-only memory 106 (e.g., non-transitory memory), random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an accelerator pedal 130 for sensing force applied by driver 132; a measurement of engine manifold pressure (MAP) from pressure sensor 121 coupled to intake manifold 44; an engine position sensor from a Hall effect sensor 118 sensing crankshaft 40 position; a measurement of air mass entering the engine from sensor 122; brake pedal position from brake pedal position sensor 154 when driver 132 applies brake pedal 150; and a measurement of throttle position from sensor 58. Barometric pressure may also be sensed (sensor not shown) for processing by controller 12. In a preferred aspect of the present description, engine position sensor 118 produces a predetermined number of equally spaced pulses every revolution of the crankshaft from which engine speed (RPM) can be determined.

Controller 12 may also broadcast vehicle information to a manufacturer via radio frequency transmitter 190. A manufacturer may receive the data via a remote receiver 191. Receiver 191 may communicate with the manufacturer via the internet or other communications system. In some examples, other engine configurations may be employed, for example a diesel engine.

During operation, each cylinder within engine 10 typically undergoes a four stroke cycle: the cycle includes the intake stroke, compression stroke, expansion stroke, and exhaust stroke. During the intake stroke, generally, the exhaust valve 54 closes and intake valve 52 opens. Air is introduced into combustion chamber 30 via intake manifold 44, and piston 36 moves to the bottom of the cylinder so as to increase the volume within combustion chamber 30. The position at which piston 36 is near the bottom of the cylinder and at the end of its stroke (e.g., when combustion chamber 30 is at its largest volume) is typically referred to by those of skill in the art as bottom dead center (BDC). During the compression stroke, intake valve 52 and exhaust valve 54 are closed. Piston 36 moves toward the cylinder head so as to compress the air within combustion chamber 30. The point at which piston 36 is at the end of its stroke and closest to the cylinder head (e.g., when combustion chamber 30 is at its smallest volume) is typically referred to by those of skill in the art as top dead center (TDC). In a process hereinafter referred to as injection, fuel is introduced into the combustion chamber. In a process hereinafter referred to as ignition, the injected fuel is ignited by known ignition means such as spark plug 92, resulting in combustion. During the expansion stroke, the expanding gases push piston 36 back to BDC. Crankshaft 40 converts piston movement into a rotational torque of the rotary shaft. Finally, during the exhaust stroke, the exhaust valve 54 opens to release the combusted air-fuel mixture to exhaust manifold 48 and the piston returns to TDC. Note that the above is shown merely as an example, and that intake and exhaust valve opening and/or closing timings may vary, such as to provide positive or negative valve overlap, late intake valve closing, or various other examples.

The system of FIG. 1 provides for an engine system, comprising: an engine; an engine air intake including an air filter, a throttle, and an intake manifold; a pressure sensor located along the engine air intake; and a controller including executable instructions stored in non-transitory memory to indicate degradation of the air filter in response to a mean pressure drop across the air filter during transient air flow through the air filter. The engine system further comprises additional instructions to determine a standard deviation of a pressure drop across the air filter. The engine system further comprises additional instructions to determine the mean pressure drop across the air filter based on output of the pressure sensor. The engine system further comprises additional instructions to estimate a useful life of the air filter based on the mean pressure drop across the air filter during transient air flow through the air filter. The engine system further comprises additional instructions to estimate a useful life of the air filter based on a standard deviation of a pressure drop across the air filter during transient air flow through the air filter. The engine system further comprises additional instructions to transmit the indication via radio frequency to an off-board device.

Figure 2:
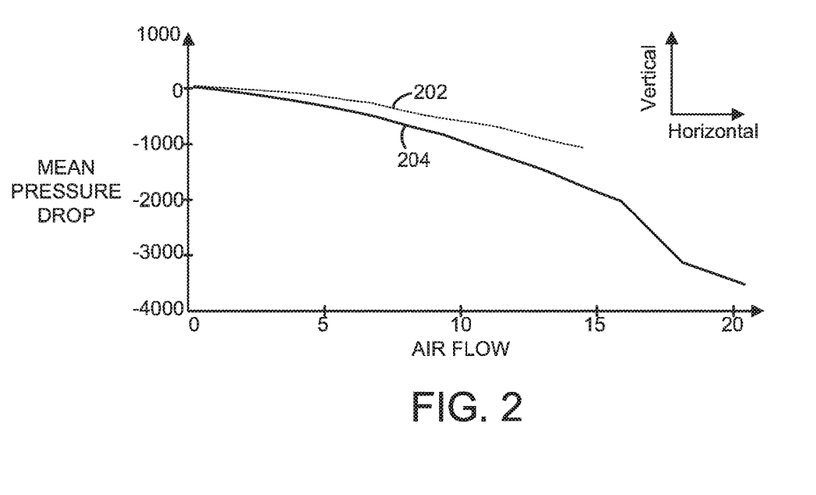
FIGS. 2 and 3 are prophetic plots of mean and standard deviation pressure drops for new and degraded air filters.

Referring now to FIG. 2, an example plot of mean air pressure drop across an engine air filter (e.g., 43 of FIG. 1) versus air flow through the engine air filter is shown in detail. The vertical axis represents mean air pressure drop across the engine air filter and the mean pressure drop increases in a direction from the top of the plot to the horizontal axis. The horizontal axis represents air flow through the engine air filter and the air flow amount increases in the direction of the horizontal axis arrow. Dotted line 202 represents mean pressure drop across a new engine air filter. Solid line 204 represents mean pressure drop across an air filter that is clogged with debris.

It may be observed that a measurable difference in the mean pressure drop between the new air filter and the clogged air filter occurs above a threshold air flow rate. The difference in the mean is more pronounced at higher air flow rates. Consequently, if a mean pressure drop across the clogged air filter at a specified air flow through the air filter divided by a mean pressure drop across the new air filter at the specified air flow is greater than a threshold, it may be determined that the clogged air filter is in a degraded state.

Figure 3:
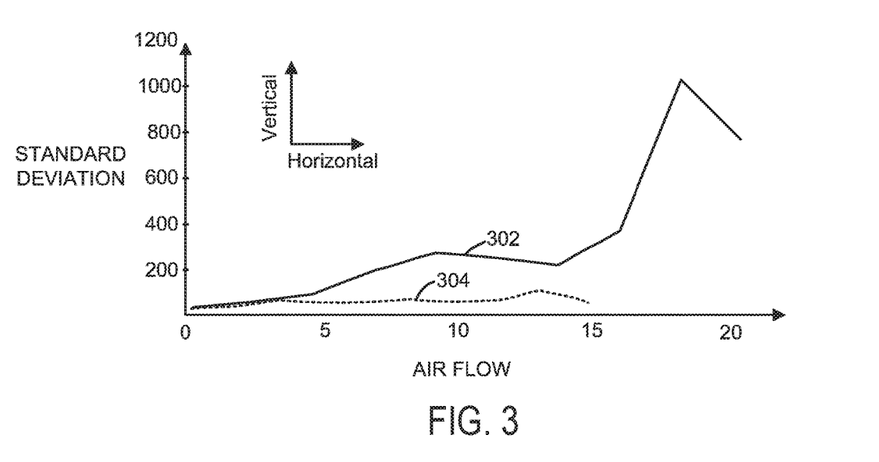
Figure 4:
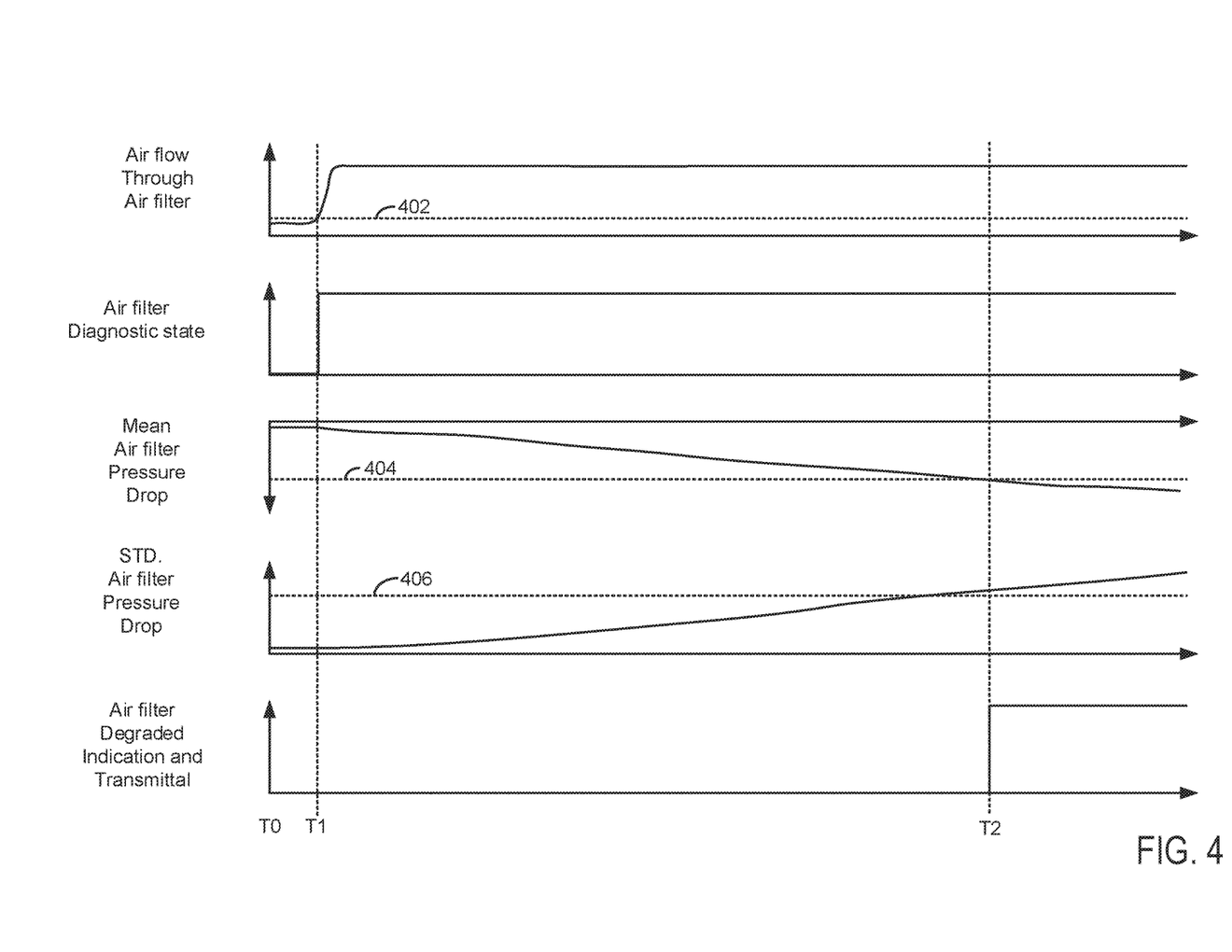
FIG. 4 is a prophetic plot of an example engine air filter diagnostic sequence.

Referring now to FIG. 3, an example plot of standard deviation of air pressure drop across an engine air filter (e.g., 43 of FIG. 1) versus air flow through the engine air filter is shown in detail. The vertical axis represents standard deviation of air pressure drop across the engine air filter and standard deviation increases in a direction of the vertical axis arrow. The horizontal axis represents air flow through the engine air filter and the air flow amount increases in the direction of the horizontal axis arrow. Dotted line 302 represents a standard deviation of pressure drop across a new engine air filter. Solid line 304 represents standard deviation of pressure drop across an air filter that is clogged with debris.

It may be observed that a measurable difference in the standard deviation of pressure drop between the new air filter and the clogged air filter occurs above a threshold air flow rate. The difference in the standard deviation in pressure drop is more pronounced at higher air flow rates. Consequently, if a standard deviation of pressure drop across the clogged air filter at a specified air flow through the air filter divided by a standard deviation of pressure drop across the new air filter at the specified air flow is greater than a threshold, it may be determined that the clogged air filter is in a degraded state.

Referring now to FIG. 4, an example plot of an air filter diagnostic sequence is shown. The diagnostic sequence may be performed via the system of FIG. 1 according to the method of FIG. 5. The plots are time aligned and occur at a same time. Vertical markers and time T0-T2 represent times of interest in the sequence.

The first plot from the top of FIG. 4 is a plot of air flow through an engine air filter versus time. The vertical axis represents air flow through the engine air filter and air flow through the engine air filter increases in the direction of the vertical axis arrow. The horizontal axis represents time and time increases from the left side of the plot to the right side of the plot. Horizontal line 402 is a minimum air flow through the engine air filter where diagnosing engine air filter performance is permitted. For example, air filter diagnostics may be performed when air flow through the air filter is above or greater than the amount of threshold 402.

The second plot from the top of FIG. 4 is a plot of engine air filter diagnostic state versus time. The vertical axis represents engine air filter diagnostic state. The engine air filter diagnostic is active when the trace is at a higher level near the vertical axis arrow. The engine air filter diagnostic is not active when the trace is at a lower level near the horizontal axis arrow. The horizontal axis represents time and time increases from the left side of the plot to the right side of the plot.

The third plot from the top of FIG. 4 is a plot of mean air filter pressure drop or mean air filter pressure difference versus time. The vertical axis represents mean air filter pressure drop and mean air filter pressure drop increases in the direction of the vertical axis arrow. The horizontal axis represents time and time increases from the left side of the plot to the right side of the plot. Horizontal line 404 is a mean air filter pressure drop magnitude above which a ratio of mean air filter pressure drop for the clogged filter divided by mean air filter pressure drop for a new air filter indicates a degraded air filter. Thus, when the mean air filter pressure drop trace is below threshold 404, the air filter is degraded from a mean air filter pressure drop perspective.

The fourth plot from the top of FIG. 4 is a plot of standard deviation of air filter pressure drop versus time. The vertical axis represents standard deviation of air filter pressure drop and standard deviation of air filter pressure drop increases in the direction of the vertical axis arrow. The horizontal axis represents time and time increases from the left side of the plot to the right side of the plot. Horizontal line 406 is a standard deviation of air filter pressure drop magnitude above which a ratio of standard deviation of air filter pressure drop for the clogged filter divided by standard deviation of air filter pressure drop for a new air filter indicates a degraded air filter. Thus, when the standard deviation of air filter pressure drop trace is above threshold 406, the air filter is degraded from a standard deviation of air filter pressure drop perspective.

The fifth plot from the top of FIG. 4 is a plot of engine air filter degradation indication state versus time. The vertical axis represents engine air filter degradation indication state. The engine air filter degradation is active when the trace is at a higher level near the vertical axis arrow. The engine air filter degradation indication state (e.g., an indication of engine air filter degradation is provided) is not active when the trace is at a lower level near the horizontal axis arrow. The horizontal axis represents time and time increases from the left side of the plot to the right side of the plot.

At time T0, air flow through the engine air filter (e.g., 43 of FIG. 1) is less than threshold 402. The air filter diagnostic is not active as indicated by the air filter diagnostic state because the air flow through the engine air filter is less than threshold 402. The mean pressure drop across the engine air filter is less than threshold 404. Likewise, the standard deviation of pressure drop across the engine air filter is less than threshold 406. Engine air filter degradation is not indicated since the air filter degradation indication state is low.

At time T1, air flow through the engine air filter increases to greater than threshold 402. Consequently, the engine air filter diagnostic is activated as indicated by the air filter diagnostic state transitioning to a higher level. The mean pressure drop across the engine air filter is less than threshold 404. Further, the standard deviation of pressure drop across the engine air filter is less than threshold 406. Engine air filter degradation is not indicated since the air filter degradation indication state is low.

Between time T1 and time T2, air flow through the engine air filter is maintained above threshold 402. The engine air filter diagnostic remains activated as indicated by the air filter diagnostic state being at a higher level. The mean pressure drop across the engine air filter increases toward threshold 404. The standard deviation of pressure drop across the engine air filter also increases toward threshold 406 and then crosses threshold 406 before time T2. These parameters indicate a trend of an increasing pressure drop across the engine air filter. The engine air filter degradation is not indicated since the air filter degradation indication state remains at a lower level. Engine air filter degradation is not indicated because both mean pressure drop across the engine air filter and standard deviation of pressure drop across the engine air filter do not exceed thresholds 404 and 406 respectively.

At time T2, the mean pressure drop across the engine air filter exceeds threshold 404, and since the standard deviation of pressure drop across the engine air filter exceeds threshold 406, air filter degradation is asserted as indicated by the air filter degradation indication state transitioning to a higher level. The engine air filter diagnostic state indicates that the engine air filter diagnostic is still active.

In this way, mean pressure drop across an engine air filter and standard deviation of pressure drop across the engine air filter may be a basis for evaluating engine air filter degradation. In other examples, only mean pressure drop across the engine air filter exceeding a threshold or only standard deviation of pressure drop across the engine air filter exceeding a threshold may be a basis for indicating engine air filter degradation.

Figure 5:
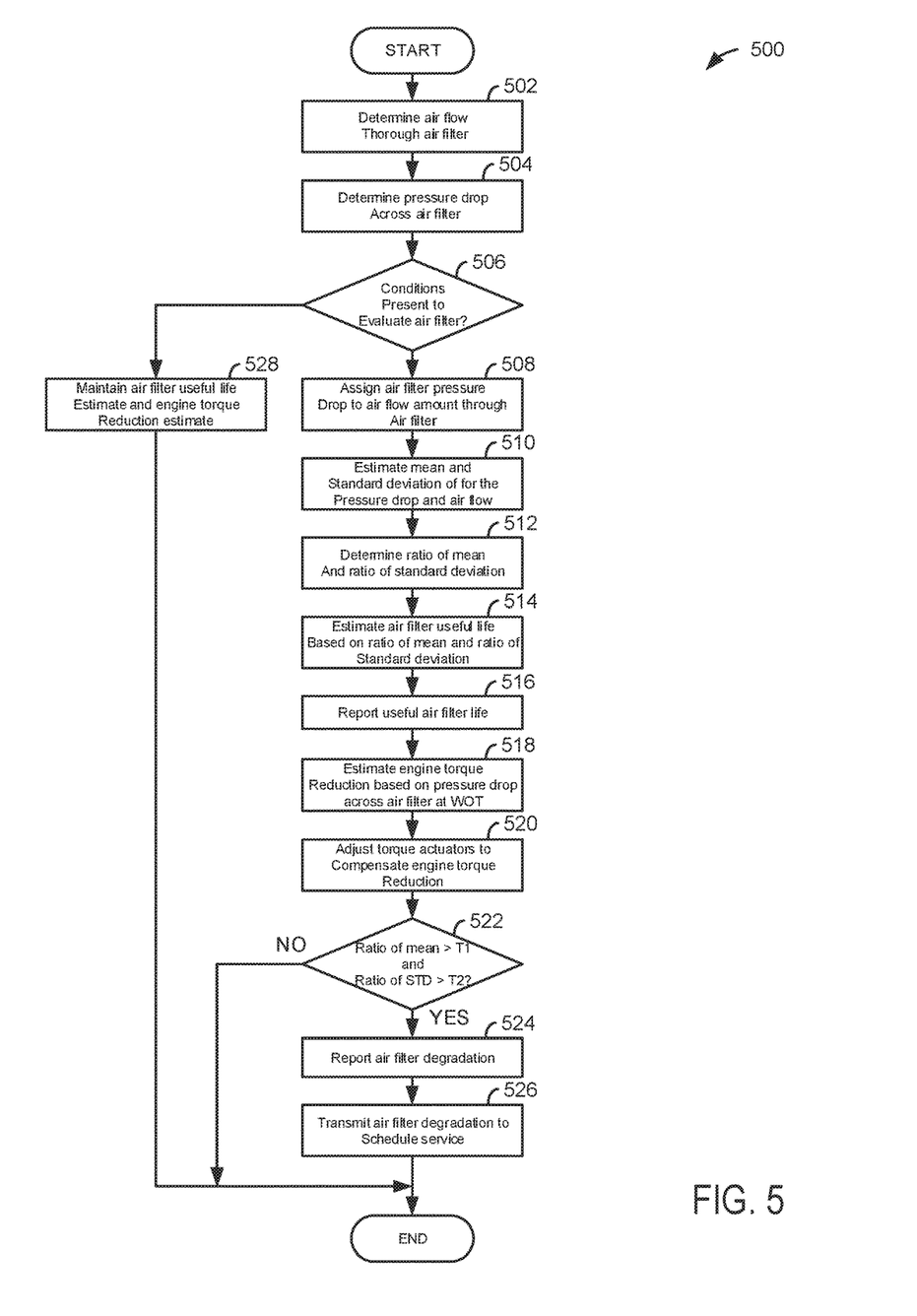
FIG. 5 is a method for diagnosing engine air filter degradation.

Referring now to FIG. 5, an example flow chart for a method for operating an engine is shown. The method of FIG. 5 may be incorporated into and may cooperate with the system of FIGS. 1 and 2. Further, at least portions of the method of FIG. 5 may be incorporated as executable instructions stored in non-transitory memory while other portions of the method may be performed via a controller transforming operating states of devices and actuators in the physical world.

At 502, method 500 determines air flow through an engine air filter. In one example, air flow through the engine air filter may be determined via output of an air flow sensor positioned in an engine air intake just downstream of the engine air filter. Method 500 proceeds to 504.

At 504, method 500 determines a pressure drop across the engine air filter. In one example, method 500 determines a pressure drop across the engine air filter via a differential or delta pressure sensor. In another example, method 500 determines the pressure drop based on subtracting a pressure downstream of the engine air filter from barometric pressure. Method 500 proceeds to 506.

At 506, method 500 judges if conditions are present to evaluate the operating state of the engine air filter. In one example, the operating conditions include air flow through the air filter being greater than a threshold air flow. Method 500 proceeds to 508.

At 528, method 500 maintains the previously determined values of engine air filter useful life and engine torque reduction amount based on mean pressure drop across the engine air filter at a predetermined air flow rate through the engine air filter. Method 500 proceeds to exit.

At 508, method 500 assigns the air filter pressure drop to an air flow amount through the engine air filter. For example, the air flow through the engine air filter is sampled at a substantially same time as the pressure drop across the engine air filter (e.g., within 500 microsecond). The pressure drop is assigned to a location in memory that corresponds to the air flow rate sampled at the time the pressure drop is sampled. The air flow rate through the engine air filter may be changing or in a transient state while the pressure drop across the engine air filter is determined. The pressure drop across the engine air filter and the air flow through the air filter may be sampled at a predetermined rate (e.g., every 100 milliseconds) and their values may be stored to memory. Method 500 proceeds to 510.

At 510, method 500 estimates the mean pressure drop corresponding to air flow through the engine air filter and the standard deviation corresponding to the air flow through the engine air filter. In one example, the mean pressure drop is determined recursively according to the following equations:

$$\mu(N) = \frac{\sum_{i=1}^{N} x_i}{N}$$

$$\mu(N+1) = \frac{\sum_{i=1}^{N+1} x_i}{N+1} = \frac{\left(\sum_{i=1}^{N} x_i\right) + x_{N+1}}{N} * \frac{N}{N+1}$$

$$= \frac{N}{N+1} * \left[\frac{\left(\sum_{i=1}^{N} x_i\right)}{N} + \frac{x_{N+1}}{N}\right]$$

$$= \frac{N}{N+1} * \left[\mu(N) + \frac{x_{N+1}}{N}\right]$$

where N is the total number of samples at the air flow rate through the engine air filter, $\mu$ is the mean value; and $x_i$ is the $i^{th}$ sample of pressure drop across the engine air filter. The standard deviation of pressure drop across the engine air filter is determined recursively according to the following equations:

$$\sigma(N) = \sqrt{\frac{\sum_{i=1}^{N}(x_i - \mu(N))^2}{N-1}} = \sigma(N) =$$

$$\sqrt{\frac{\sum_{i=1}^{N+1}(x_i - \mu(N+1))^2}{N}} = \sigma(N+1)^2 = \sqrt{\frac{\sum_{i=1}^{N+1}(x_i - \mu(N+1))^2}{N}} =$$

$$\sigma(N+1)^2 = \frac{\sum_{i=1}^{N+1}(x_i - \mu(N+1))^2 + (x_{N+1} - \mu(N+1))^2}{N-1}\left(\frac{N-1}{N}\right)$$

For large $N$: $\mu(N+1) \sim \mu(N)$ $$\sigma(N+1)^2 \sim \frac{\sum_{i=1}^{N}(x_i - \mu(N))^2 + (x_{N+1} - \mu(N+1))^2}{N-1}$$

$$\left(\frac{N-1}{N}\right) \sim \left[\sigma(N)^2 + \frac{(x_{N+1} - \mu(N+1))^2}{N-1}\right]\left(\frac{N-1}{N}\right)$$

Method 500 proceeds to 510 after determining the mean and standard deviations of pressure drops across the engine air filter corresponding to air flow through the engine air filter. The mean and standard deviation for a plurality of air flows are determined and stored to memory.

At 512, method 500 determines mean pressure drop ratios and standard deviation pressure drop ratios for the plurality of air flow amounts through the engine air filter. The mean pressured drop ratio for each air flow rate through the air filter is the mean pressure drop for an air flow rate through the air filter determined at 510 divided by the mean pressure drop for the respective air flow rates though a new air filter. For example, the mean pressure drop ratio for air flow X though the air filter is mean pressure drop at X air flow rate through the air filter for the present air filter divided by mean pressure drop at X air flow rate through a new air filter, which may be expressed as:

$$\mu_{mean\_ratioX} = \frac{\mu_{meanX}}{\mu_{mean\_newX}}$$

where $\mu_{mean\_ratioX}$ is the mean pressure drop ratio a X flow rate through the engine air filter, $\mu_{meanX}$ is the mean pressure drop across the air filter when air flows through the air filter at a rate of X (determined at 510), $\mu_{mean\_newX}$ is the mean pressure drop across a new air filter when air flows through the new air filter at a rate of X. For a different flow rate Y though the air filter the mean pressure drop may be expressed as:

$$\mu_{mean\_ratioY} = \frac{\mu_{meanY}}{\mu_{mean\_newY}}$$

where $\mu_{mean\_ratioY}$ is the mean pressure drop ratio a Y flow rate through the engine air filter, $\mu_{meanY}$ is the mean pressure drop across the air filter when air flows through the air filter at a rate of Y (determined at 510), $\mu_{mean\_newY}$ is the mean pressure drop across a new air filter when air flows through the new air filter at a rate of Y.

The standard deviation pressured drop ratio for each air flow rate through the air filter is the standard deviation pressure drop for an air flow rate through the air filter determined at 510 divided by the standard deviation pressure drop for the respective air flow rates though a new air filter. For example, the standard pressure drop ratio for air flow X though the air filter is standard deviation pressure drop at X air flow rate through the air filter for the present air filter divided by standard deviation pressure drop at X air flow rate through a new air filter, which may be expressed as:

$$\mu_{std\_ratioX} = \frac{\mu_{stdX}}{\mu_{std\_newX}}$$

where $\mu_{std\_ratioX}$ is the standard deviation pressure drop ratio a X flow rate through the engine air filter, $\mu_{stdX}$ is the standard deviation pressure drop across the air filter when air flows through the air filter at a rate of X (determined at 510), $\mu_{std\_newX}$ is the standard deviation pressure drop across a new air filter when air flows through the new air filter at a rate of X. For a different flow rate Y though the air filter the standard deviation pressure drop may be expressed as:

$$\mu_{std\_ratioY} = \frac{\mu_{stdY}}{\mu_{std\_newY}}$$

where $\mu_{std\_ratioY}$ is the standard deviation pressure drop ratio a Y flow rate through the engine air filter, $\mu_{stdY}$ is the standard deviation pressure drop across the air filter when air flows through the air filter at a rate of Y (determined at 510), $\mu_{std\_newY}$ is the standard deviation pressure drop across a new air filter when air flows through the new air filter at a rate of Y. The mean ratio and standard deviation ratio for each flow rate though the air filter that is stored in memory is determined. In some examples, one standard deviation pressure drop ratio and one mean pressure drop ratio for a single flow rate is determined. In other examples, N (e.g., where N is an integer variable) standard deviation pressure drops ratio and N mean pressure drop ratios for N flow rates are determined. Method 500 proceeds to 514.

At 514, method 500 estimates the useful life of the engine air filter. The useful life estimate may be based off a predetermined air flow rate through the air filter via the following equations:

$$\% \, life1 = \left(\frac{\mu_{actualX}}{\mu_{newX}} - 1\right) * \frac{1}{T_{\mu X} - 1}$$

where % life1 is the value of the estimated useful life of the air filter based on the mean pressure drop at X air flow though the engine air filter, $\mu_{actualX}$ is the actual mean pressure drop across the air filter at X flow through the air filter for the air filter being used, $\mu_{newX}$ is the mean pressure drop across a new air filter at X flow through the new air filter, $T_{\mu X}$ is an empirically determined threshold mean pressure drop that indicates a degraded air filter for a flow rate of X through the air filter. The useful life estimate includes a second equation:

$$\% \, life2 = \left(\frac{\sigma_{actualX}}{\sigma_{newX}} - 1\right) * \frac{1}{T_{\sigma X} - 1}$$

where % life2 is the value of the estimated useful life of the air filter based on the standard deviation of pressure drop at X air flow though the engine air filter, $\sigma_{actualX}$ is the actual standard deviation pressure drop across the air filter at X flow through the air filter for the air filter being used, $\sigma_{newX}$ is the standard deviation pressure drop across a new air filter at X flow through the new air filter, $T_{\sigma X}$ is an empirically determined threshold standard deviation pressure drop that indicates a degraded air filter for a flow rate of X through the air filter. The estimate of useful air filter life is determined by:

% life=min(% life1,% life2)

where % life is the estimate of useful air filter life and it is based on the minimum value of the two values % life1 and % life2. If desired, useful life values for each flow rate through the air filter stored in memory may be determined and the minimum value of the plurality of values may be indicated as the useful air filter life. Method 500 proceeds to 516.

At 516, method 500 reports the useful life to the driver. The useful life may be reported to the driver via a human/machine interface. Method 500 proceeds to 518.

At 518, method 500 estimates engine torque reductions for the engine based on the pressure drop across the air filter at wide open throttle or the engine air flow rate at wide open throttle (WOT). In one example, a table or function outputs a torque value that is a torque loss for the engine when the engine is operated at WOT. The values stored in the table are empirically determined and the table or function is indexed via engine speed and engine air flow at WOT based on data from the present air filter. Method 500 proceeds to 520.

At 520, method 500 adjusts driveline torque actuators to compensate for engine torque reduction related to the engine air filter. In one example, method 500 increases output of an electric machine to provide a desired torque when the engine is producing less than rated torque due to a clogged air filter. The electric machine may be an integrated starter/generator, a belt driven integrated starter/generator or another motor/generator in the driveline. For example, if the driver is requesting 300 N-m and the engine outputs 310 N-m at the same engine speed with a new air filter, the engine may provide the driver requested torque when the air filter is new. However, if the engine produces 290 N-m at the same engine speed when the air filter is partially clogged, the electric machine outputs the 10 N-m to compensate for the rejection in engine torque. Further, at lighter driver demand torque requests, the engine throttle may be opened more when the air filter is partially clogged as compared to operating at the same engine speed and driver demand when the air filter is new. Fuel injectors and cam timing may also be adjusted to compensate for the plugged air filter so that the driver applies the accelerator pedal in a same way for a same torque request during same conditions when the air filter is new or clogged. Method 500 proceeds to 522.

At 522, method 500 judges if the mean pressure drop across the present engine air filter at a predetermined flow rate through the present engine air filter divided by the mean pressure drop across a new engine air filter at the predetermined flow rate (e.g., the mean pressure drop ratio) is greater than a first threshold value. Method 500 also judges if the standard deviation of pressure drop across the present engine air filter at the predetermined flow rate through the present engine air filter divided by the standard deviation of pressure drop across a new engine air filter at the present predetermined air flow rate through the new engine air filter (e.g., the standard deviation pressure drop ratio) is greater than a second threshold value. If the present mean pressure drop ratio is greater than the first threshold and the standard deviation pressure drop ratio is greater than the second threshold, the answer is yes and method 500 proceeds to 524. Otherwise, the answer is no and method 500 proceeds to exit.

At 524, method 500 reports air filter degradation to the vehicle driver. The vehicle driver may be notified of air filter degradation and useful life via a human/machine interface. Method 500 proceeds to 526.

At 526, method 500 transmits the air filter degradation status and useful life data off-board to a manufacturer via radio frequency transmitter. By transmitting the air filter degradation off-board the vehicle, a service appointment may be scheduled at a manufacturer's representative so that vehicle performance may be restored to nominal levels. Further, if desired, a new air filter may be ordered based on the data transmitted by the vehicle to the manufacturer. Method 500 proceeds to exit.

Thus, the method of FIG. 5 provides for an engine air filter diagnostic method, comprising: indicating via a controller, engine air filter degradation in response to a mean of a pressure change across an engine air filter, the pressure change across the engine air filter based on data observed via the controller during transient air flow conditions through the engine air filter. The method includes where the mean of the pressure change across the engine air filter is determined via a differential pressure sensor. The method includes where the data observed via the controller during transient air flow conditions through the engine air filter is provided via a mass air flow sensor. The method includes where indicating includes transmitting data off board a vehicle in which the engine air filter resides via radio frequency. The method includes where indicating includes displaying a condition of engine air filter degradation to a driver via a human/machine interface. The method further comprises estimating a useful life of the engine air filter based on the mean. The method further comprises estimating the useful life of the engine air filter based additionally on a standard deviation of the pressure change across the engine air filter.

The method of FIG. 5 also provides for an engine air filter diagnostic method, comprising: indicating via a controller, air filter degradation in response to a mean of a pressure change across an engine air filter and a standard deviation of the pressure change across the engine air filter, the pressure change across the engine air filter based on data observed via the controller during conditions where air is flowing through the engine air filter. The method further comprises estimating a useful life of the engine air filter based on the mean. The method further comprises estimating a useful life of the engine air filter based on the standard deviation. The method includes where the indication is based on the mean exceeding a threshold. The method includes where the indication is based on the standard deviation exceeding a threshold. The method includes where the mean is recursively estimated. The method includes where the standard deviation is recursively estimated.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, at least a portion of the described actions, operations and/or functions may graphically represent code to be programmed into non-transitory memory of the computer readable storage medium in the control system. The control actions may also transform the operating state of one or more sensors or actuators in the physical world when the described actions are carried out by executing the instructions in a system including the various engine hardware components in combination with one or more controllers.

This concludes the description. The reading of it by those skilled in the art would bring to mind many alterations and modifications without departing from the spirit and the scope of the description. For example, I3, I4, I5, V6, V8, V10, and V12 engines operating in natural gas, gasoline, diesel, or alternative fuel configurations could use the present description to advantage.

The invention claimed is:

1. An engine air filter diagnostic method, comprising:
indicating via a controller, engine air filter degradation in response to a mean of a pressure change across an engine air filter, the pressure change across the engine air filter based on data observed via the controller during transient air flow conditions through the engine air filter; and
adjusting one or more engine torque actuators to compensate for engine torque reduction related to the engine air filter degradation.

2. The method of claim 1, where the mean of the pressure change across the engine air filter is determined via a differential pressure sensor.

3. The method of claim 1, where the data observed via the controller during transient air flow conditions through the engine air filter is provided via a mass air flow sensor.

4. The method of claim 1, wherein the adjusting the one or more engine torque actuators comprises increasing power output of an electric machine configured to provide torque to a crankshaft, when an engine throttle is commanded to a fully open position.

5. The method of claim 1, wherein the adjusting the one or more engine torque actuators comprises commanding an engine throttle to a more open position.

6. The method of claim 1, further comprising estimating a useful life of the engine air filter based on the mean pressure change across the engine air filter, wherein the mean pressure change is determined recursively for pressure changes sampled at air flow rates within a threshold range, and wherein the estimating the useful life of the engine air filter is further based on a comparison between the mean pressure change and a predetermined mean pressure change for a healthy filter at air flow rates within the threshold range.

7. The method of claim 6, further comprising estimating the useful life of the engine air filter based additionally on a standard deviation of the pressure change across the engine air filter, wherein the standard deviation of the pressure change across the engine air filter is determined recursively for pressure changes sampled at air flow rates within the threshold range, and wherein the estimating the useful life of the engine air filter is further based on a comparison between the recursively determined standard deviation and a predetermined standard deviation for a healthy filter at air flow rates within the threshold range.

8. An engine air filter diagnostic method, comprising:
indicating via a controller, air filter degradation in response to a mean of a pressure change across an engine air filter and a standard deviation of the pressure change across the engine air filter, the pressure change across the engine air filter based on data observed via the controller during conditions where air is flowing through the engine air filter; and
adjusting one or more engine torque actuators to compensate for engine torque reduction related to the air filter degradation.

9. The method of claim 8, further comprising estimating a useful life of the engine air filter based on one or more of the mean and standard deviation.

10. The method of claim 8, further comprising estimating an amount of engine torque reduction related to the air filter degradation based on a difference between a measured air flow rate through the engine air filter at wide open throttle, and a reference air flow rate at wide open throttle for a healthy engine air filter.

11. The method of claim 8, where the indication is based on the mean exceeding a threshold.

12. The method of claim 8, where the indication is based on the standard deviation exceeding a threshold.

13. The method of claim 8, where the mean is recursively estimated for pressure changes sampled at a plurality of air flow rate ranges, wherein the mean is recursively estimated separately for each of the plurality of air flow rate ranges, such that the mean comprises a plurality of mean estimates, each of the plurality of mean estimates corresponding to a distinct air flow rate range, wherein each of the plurality of mean estimates is based on pressure changes sampled at air flow rates within the corresponding distinct air flow rate range.

14. The method of claim 8, where the standard deviation is recursively estimated for pressure changes sampled at a plurality of air flow rate ranges, wherein the standard deviation is recursively estimated separately for each of the plurality of air flow rate ranges, such that the standard deviation comprises a plurality of standard deviation estimates, each of the plurality of standard deviation estimates corresponding to a distinct air flow rate range, wherein each of the plurality of standard deviation estimates is based on pressure changes sampled at air flow rates within the corresponding distinct air flow rate range.

15. An engine system, comprising:
an engine;
an engine air intake including an air filter, a throttle, and an intake manifold;
a pressure sensor located along the engine air intake; and
a controller including executable instructions stored in non-transitory memory to:
indicate degradation of the air filter in response to a mean pressure drop across the air filter during transient air flow through the air filter; and
adjust one or more engine torque actuators to compensate for engine torque reduction related to air filter degradation.

16. The engine system of claim 15, further comprising additional instructions to determine a standard deviation of a pressure drop across the air filter.

17. The engine system of claim 15, further comprising additional instructions to determine the mean pressure drop across the air filter based on output of the pressure sensor.

18. The engine system of claim 15, further comprising additional instructions to estimate a useful life of the air filter based on the mean pressure drop across the air filter during transient air flow through the air filter.

19. The engine system of claim 15, further comprising additional instructions to estimate a useful life of the air filter based on a standard deviation of a pressure drop across the air filter during transient air flow through the air filter.

20. The engine system of claim 15, further comprising additional instructions to transmit the indication via radio frequency to an off-board device.

* * * * *